US012023202B2

United States Patent
Seth et al.

(10) Patent No.: US 12,023,202 B2
(45) Date of Patent: Jul. 2, 2024

(54) METHODS AND SYSTEMS FOR ACQUIRING COMPOSITE 3D ULTRASOUND IMAGES

(71) Applicant: KONINKLIJKE PHILIPS N.V., Eindhoven (NL)

(72) Inventors: Subhendu Seth, Bangalore (IN); Celine Firtion, Surat (IN); Pallavi Vajinepalli, Bangalore (IN); David Nigel Roundhill, Woodinville, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 364 days.

(21) Appl. No.: 17/436,713

(22) PCT Filed: Mar. 6, 2020

(86) PCT No.: PCT/EP2020/056051
§ 371 (c)(1),
(2) Date: Sep. 7, 2021

(87) PCT Pub. No.: WO2020/182670
PCT Pub. Date: Sep. 17, 2020

(65) Prior Publication Data
US 2022/0167947 A1 Jun. 2, 2022

Related U.S. Application Data

(60) Provisional application No. 62/815,484, filed on Mar. 8, 2019.

(30) Foreign Application Priority Data

Mar. 18, 2019 (EP) ..................... 19163454

(51) Int. Cl.
*A61B 8/08* (2006.01)
*A61B 8/00* (2006.01)
*G06N 20/00* (2019.01)

(52) U.S. Cl.
CPC ............ *A61B 8/5253* (2013.01); *A61B 8/469* (2013.01); *A61B 8/483* (2013.01); *A61B 8/5223* (2013.01); *A61B 8/5276* (2013.01); *G06N 20/00* (2019.01)

(58) Field of Classification Search
CPC ... A61B 8/466; A61B 8/463; A61B 2090/378; A61B 8/469; A61B 8/483; A61B 8/5238;
(Continued)

(56) References Cited

U.S. PATENT DOCUMENTS

| 5,575,286 A | 11/1996 | Weng et al. |
| 5,997,479 A | 12/1999 | Savord et al. |

(Continued)

FOREIGN PATENT DOCUMENTS

| EP | 2807978 A1 | 12/2014 |
| WO | 2018099810 A1 | 6/2018 |

OTHER PUBLICATIONS

Dyer et al: F;A Clinical System for Three-Dimensional Extended-Field0of-View Ultrasound; The British Journal of Radiology, 85(2012) pp. e919-e924.

(Continued)

*Primary Examiner* — Gerald Johnson

(57) ABSTRACT

The invention provides for a method of obtaining a composite 3D ultrasound image of a region of interest. The method includes obtaining preliminary ultrasound data from a region of interest of a subject and identifying an anatomical feature within the region of interest based on the preliminary ultrasound data. A first imaging position and one or more additional imaging positions are then determined based on the anatomical feature. A first 3D ultrasound image is obtained from the first imaging position and one or more additional 3D ultrasound images are obtained from the one or more additional imaging positions, wherein a portion of (Continued)

the first 3D ultrasound image overlaps a portion of the one or more additional 3D ultrasound images, thereby forming an overlapping portion comprising the anatomical feature. Spatial registration is performed between the first 3D ultrasound image and the one or more additional 3D ultrasound images based on the anatomical feature the 3D ultrasound images are then blended based on the spatial registration, thereby generating a composite 3D ultrasound image.

20 Claims, 4 Drawing Sheets

(58) Field of Classification Search
CPC ............ A61B 8/5223; A61B 2034/102; G06T 2207/10028
See application file for complete search history.

(56) References Cited

U.S. PATENT DOCUMENTS

| | | | |
|---|---|---|---|
| 6,013,032 | A | 1/2000 | Savord |
| 6,283,919 | B1 | 9/2001 | Roundhill et al. |
| 6,458,083 | B1 | 10/2002 | Jago et al. |
| 10,248,981 | B1* | 4/2019 | Dallas ................ G06Q 30/0643 |
| 2007/0255137 | A1* | 11/2007 | Sui ...................... G01S 15/8993 600/443 |
| 2013/0035596 | A1 | 2/2013 | Ionasec et al. |
| 2013/0289407 | A1* | 10/2013 | Lee ........................ A61B 8/145 600/443 |
| 2014/0193053 | A1* | 7/2014 | Kadoury ................ A61B 90/36 382/128 |
| 2015/0133784 | A1* | 5/2015 | Kapoor ................ A61B 8/5246 600/438 |
| 2017/0181730 | A1* | 6/2017 | Ardon ................. G01S 15/8925 |
| 2017/0325783 | A1* | 11/2017 | White .................... G16H 50/30 |
| 2018/0049721 | A1* | 2/2018 | Ben-Lavi .................. G06T 7/12 |
| 2019/0069882 | A1* | 3/2019 | Moctezuma de la Barrera .......... G06T 7/33 |
| 2021/0219961 | A1* | 7/2021 | Toyonaga ............ A61B 8/5253 |

OTHER PUBLICATIONS

Elbaz et al: "3D Point Cloud Registration for Localization Using a Deep Neural Network Auto-Encoder"; 2017 IEEE Conference on Computer Vision and Pattern Recognition; pp. 2471-2481.

Flach et al: "Pure:Panoramic Ultrasound Reconstruction by Seamless Stitching of Volumes"; Published in Sasimi@ICCAI, 2016, pp. 1-10.

Huang et al: "Non-Rigid Registration Under Isometric Deformations"; Eurographics Symposium on Gemoetry Processing, 2008, vol. 27 (2008), No. 5, pp. 1449-1457.

PCT/EP2020/056051, ISR & Written Opinion, dated Apr. 2, 2020.

Kutarnia: "A Markov Random Field Based Approach to 3D Mosaicing and Registration Applied to Ultrasound Simulation"; Medical Image Analysis 24 (2015) pp. 106-204.

Poon et al: "Three-Dimensional Extended Field-Of-View Ultrasound"; Ultrasound in Med. & Biol., vol. 32, No. 3, pp. 357-369, 2006.

Rajpoot et al:"Multiview Fusion 3-D Echocardiography: Improving the Information and Quality of Real-Time 3-D Echocardiography"; Ultrasound in Med. & Biol., vol. 37, No. 7, 2011, pp. 1056-1072.

Wachinger: "Ultrasound Mosaicing and Motion Modeling: Applications in Medical Image Registration"; Dissertaion, Technische Universitat Munche, 2011, 263 Page Document.

Kutarnia: "A Markov Random Field Based Approach to 3D Mosaicing and Registration Applied to Ultrasound Simulation"; Worcester Polytechic Institute, Dissertation, 2014, 204 Pages.

* cited by examiner

METHODS AND SYSTEMS FOR ACQUIRING COMPOSITE 3D ULTRASOUND IMAGES

CROSS-REFERENCE TO PRIOR APPLICATIONS

This application is the U.S. National Phase application under 35 U.S.C. § 371 of International Application No. PCT/EP2020/056051, filed on Mar. 6, 2020, which claims the benefit of U.S. Provisional Patent Application No. 62/815,484, filed on Mar. 8, 2019 and European Patent Application No. 19163454.2, filed on Mar. 18, 2019. These applications are hereby incorporated by reference herein.

FIELD OF THE INVENTION

The invention relates to the field of ultrasound imaging, and in particular to the field of composite ultrasound imaging.

BACKGROUND OF THE INVENTION

Typical ultrasound examination is limited by a small field of view due to physical and engineering constraints. In order to overcome this limitation, composite ultrasound imaging has been developed, whereby a series of ultrasound images is stitched together to form a composite ultrasound image with a larger field of view.

For example, in 3D ultrasound imaging, stitching a series of 3D ultrasound images may be used to visualize large organs (or a complete fetus) or organs in the context of their neighboring anatomical regions. This may bring several potential clinical advantages, such as visualizing large anatomical structures, for example a gravid uterus (womb with fetus, placenta and amniotic fluid) which is impossible to capture in a single volume acquisition in the second and third trimesters of pregnancy as described in Dyer et al., A clinical system for three-dimensional extended-field-of-view ultrasound, Br J Radiol., 85(1018), 2012, pp. 919-924.

Several research papers discuss numerous sophisticated algorithms for stitching volumes using the image data alone, such as Rajpoot et al., Multi-view fusion 3-D echocardiography: improving the information and quality of real-time 3-D echocardiography, Ultrasound Med Bio, 37, 2011, pp. 1056-72.

However, the existing techniques often result in an inaccurate view of the region of interest. In addition, the movement of an object of interest, or incorrect probe placement, can reduce the image quality of the final composite image.

There is therefore a need for a means of acquiring an accurate and robust composite ultrasound image.

Document EP 2,807,978 discloses a method of obtaining a composite 3D model using 3D ultrasound imaging.

SUMMARY OF THE INVENTION

The invention is defined by the claims.

According to examples in accordance with an aspect of the invention, there is provided a method for obtaining a composite 3D ultrasound image of a region of interest, the method comprising:
obtaining preliminary ultrasound data from a region of interest of a subject; identifying an anatomical feature within the region of interest based on the preliminary ultrasound data;
determining a first imaging position and one or more additional imaging positions based on the anatomical feature;
obtaining a first 3D ultrasound image from the first imaging position and one or more additional 3D ultrasound images from the one or more additional imaging positions, wherein a portion of the first 3D ultrasound image overlaps a portion of the one or more additional 3D ultrasound images, thereby forming an overlapping portion and wherein the overlapping portion comprises the anatomical feature;
performing spatial registration between the first 3D ultrasound image and the one or more additional 3D ultrasound images based on the anatomical feature; and
blending the first 3D ultrasound image and the one or more additional 3D ultrasound images based on the spatial registration, thereby generating a composite 3D ultrasound image.

The method provides for a means of obtaining a composite 3D ultrasound image.

Ultrasound imaging is typically limited to a confined field of view. By stitching multiple ultrasound images, for example 3D ultrasound images, together it is possible to extend the field of view. However, conventional methods for stitching multiple 3D ultrasound images are very susceptible to image artifacts.

By blending the 3D ultrasound images based on an anatomical feature, it is possible to reduce the number of image artifacts in the final composite image, thereby improving the accuracy of the composite 3D ultrasound image.

The preliminary ultrasound data is acquired in order to guide the acquisition of the 3D ultrasound images such that they contain the anatomical feature of interest.

In an embodiment, the method further comprises determining a motion of the anatomical feature based on the composite 3D ultrasound image.

In this way, motion may be accounted for when generating the composite 3D ultrasound image.

In a further embodiment, determining the motion of the anatomical feature comprises:
applying a non-rigid transformation matrix to the composite 3D ultrasound image; and
identifying an artifact based on the transformed composite 3D ultrasound image.

In this way, motion may be detected based on motion artifacts generated by the transformation matrix.

In a further embodiment, determining the motion of the anatomical feature comprises tracking the artifact.

In this way, the motion of an anatomical feature over time may be monitored.

In an arrangement, performing spatial registration comprises generating a 3D point cloud within the first 3D ultrasound image and the one or more additional 3D ultrasound images, wherein the 3D point cloud represents a surface within the first 3D ultrasound image and a surface within the one or more additional 3D ultrasound images.

In this way, the various surfaces within the 3D ultrasound images may be represented by a series of points distributed across the virtual space. In this way, anatomical features within the 3D images may be recognized based on the distribution of the points.

In an embodiment, performing spatial registration comprises using a machine learning algorithm.

In this way, the spatial registration may be performed using machine learning techniques, for example, by recognizing anatomical features within the 3D ultrasound images.

In an embodiment, the machine learning algorithm is adapted to perform bi-level stitching based on the 3D point cloud.

In an arrangement, performing spatial registration further comprises generating a probability map based on the 3D point cloud, the probability map representing a confidence value of the anatomical feature occupying a given point within the first 3D ultrasound image and the one or more additional 3D ultrasound images.

In this way, the location of an anatomical feature within the 3D ultrasound images may be represented by a probability map, which represents the likelihood of the anatomical feature being located at a given point based on the 3D point cloud.

In a further embodiment, performing spatial registration comprises identifying a location of the anatomical feature within the first 3D ultrasound image and the one or more additional 3D ultrasound images when the confidence value is greater than a predetermined value.

The confidence threshold may be varied according to the desired accuracy of the given application.

In an arrangement, blending the first 3D ultrasound image and the one or more additional 3D ultrasound images comprises generating a 3D confidence map of the overlapping portion based on the probability map.

In this way, the likelihood of finding the anatomical feature within the overlapping portion of the 3D ultrasound images may be used as an input to the blending algorithm.

In an embodiment, blending the first 3D ultrasound image and the one or more additional 3D ultrasound images comprises applying Poisson blending the first 3D ultrasound image and the one or more additional 3D ultrasound images.

According to examples in accordance with an aspect of the invention, there is provided a computer program comprising computer program code means which is adapted, when said computer program is run on a computer, to implement the method described above.

According to examples in accordance with an aspect of the invention, there is provided a processing unit, wherein the processing unit is adapted to:
obtain preliminary ultrasound data from a region of interest of a subject;
identify an anatomical feature within the region of interest based on the preliminary ultrasound data;
determine a first imaging position and one or more additional imaging positions based on the anatomical feature;
obtain a first 3D ultrasound image from the first imaging position and one or more additional 3D ultrasound images from the one or more additional imaging positions, wherein a portion of the first 3D ultrasound image overlaps a portion of the one or more additional 3D ultrasound images, thereby forming an overlapping portion and wherein the overlapping portion comprises the anatomical feature;
perform spatial registration between the first 3D ultrasound image and the one or more additional 3D ultrasound images based on the anatomical feature; and
blend the first 3D ultrasound image and the one or more additional 3D ultrasound images based on the spatial registration, thereby generating a composite 3D ultrasound image.

According to examples in accordance with an aspect of the invention, there is provided an ultrasound system, the system comprising:
a processing unit as described above; and
an ultrasound probe adapted to acquire the 4D ultrasound data.

In an embodiment, the ultrasound probe comprises one or more of
a motion sensor;
an electromagnetic tracker; and
a leap tracker.

These trackers may help to reduce, or eliminate, motion artifacts caused by the probe or external movement of the subject, thereby isolating the motion to within the imaging region.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
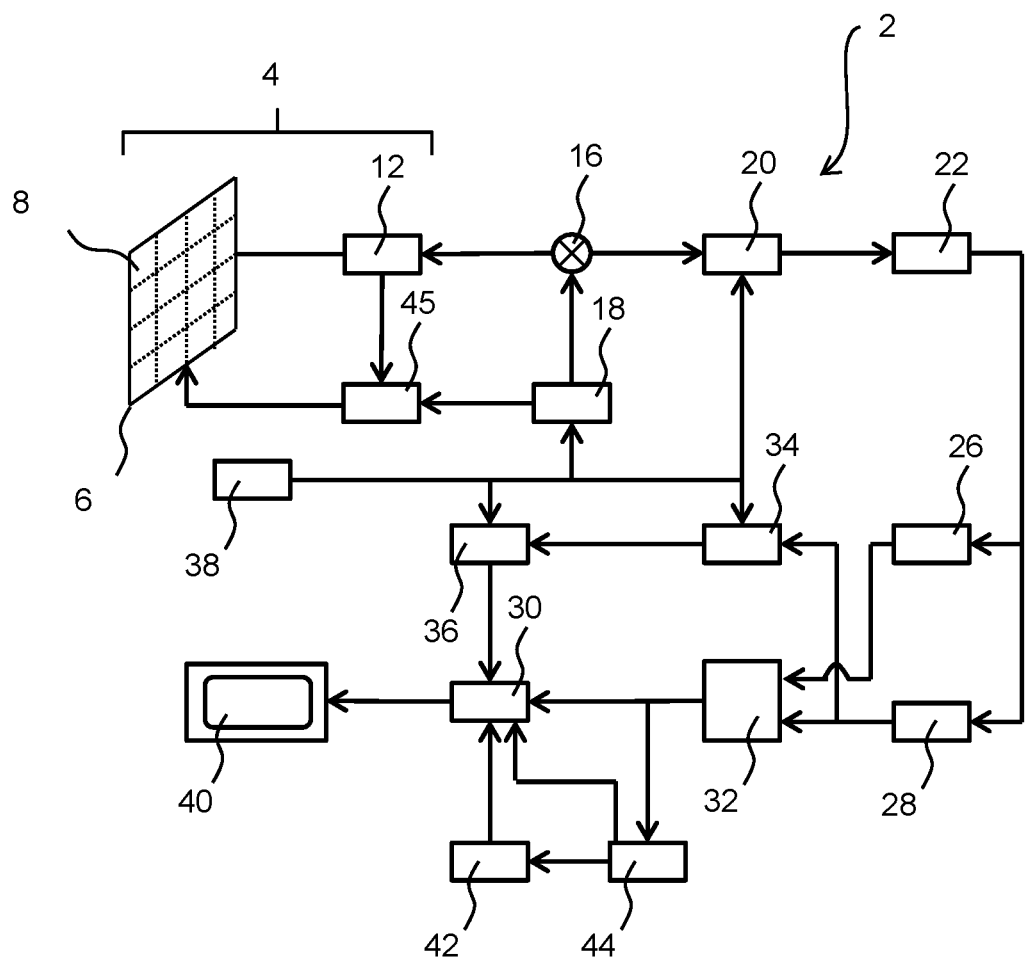
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides for a method of obtaining a composite 3D ultrasound image of a region of interest. The method includes obtaining preliminary ultrasound data from a region of interest of a subject and identifying an anatomical feature within the region of interest based on the preliminary ultrasound data. A first imaging position and one or more additional imaging positions are then determined based on the anatomical feature. A first 3D ultrasound image is obtained from the first imaging position and one or more additional 3D ultrasound images are obtained from the one or more additional imaging positions, wherein a portion of the first 3D ultrasound image overlaps a portion of the one or more additional 3D ultrasound images, thereby forming an overlapping portion comprising the anatomical feature. Spatial registration is performed between the first 3D ultrasound image and the one or more additional 3D ultrasound images based on the anatomical feature the 3D ultrasound images are then blended based on the spatial registration, thereby generating a composite 3D ultrasound image.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The transducer controller 18 can include transmission circuitry arranged to drive the transducer elements of the transducer array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the beamformer 12 and the main beamformer 20, which are adapted to receive signals are shown, for simplicity. In the complete system, there will also be a transmission chain with a transmission micro beamformer, and a main transmission beamformer.

The function of the microbeamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user interface 38, such as the point in the anatomy of an image where a measurement is to be made.

Output data from the quantification processor is coupled to a graphics processor 36 for the reproduction of measurement graphics and values with the image on the image display 40, and for audio output from the image display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transducer controller 18 to control the generation of ultrasound signals from the transducer array 6 and hence the images produced by the transducer array and the ultrasound system. The transmit control function of the transducer controller 18 is only one of the functions performed. The transducer controller 18 also takes account of the mode of operation (given by the user) and the corresponding required transmitter configuration and band-pass configuration in the receiver analog to digital converter. The transducer controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

The methods described herein may be performed on a processing unit. Such a processing unit may be located within an ultrasound system, such as the system described above with reference to FIG. 1. For example, the image processor 30 described above may perform some, or all, of the method steps detailed below. Alternatively, the processing unit may be located in any suitable system, such as a monitoring system, that is adapted to receive an input relating to a subject.

Figure 2:
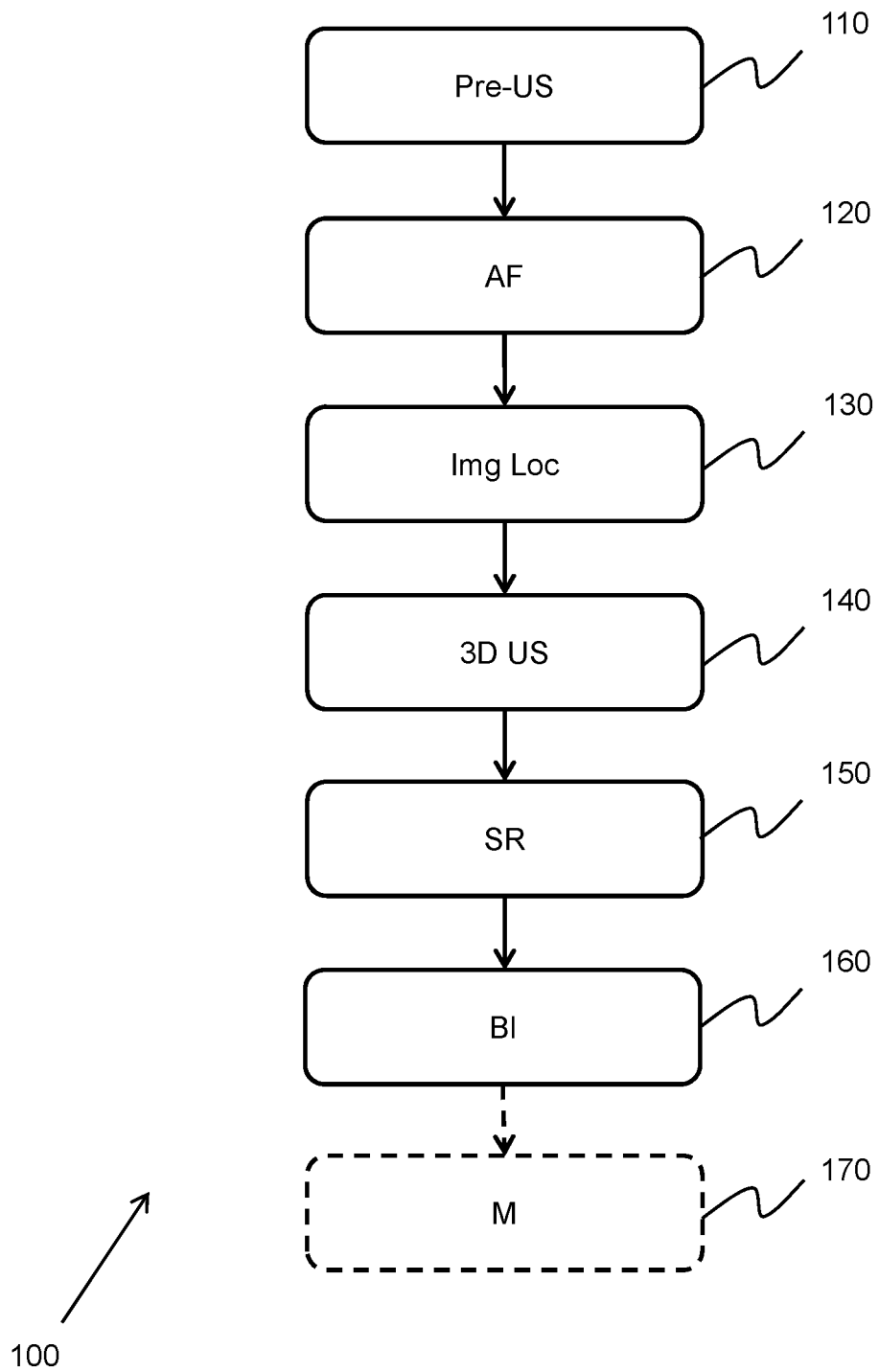
FIG. 2 shows a method of the invention.

FIG. 2 shows a method 100 for obtaining a composite 3D ultrasound image of a region of interest.

The method begins in step 110 by obtaining preliminary ultrasound data from a region of interest of a subject.

An initial scouting scan is performed in order to obtain preliminary ultrasound data from a region of interest. This scouting scan may be performed using any ultrasound probe and the preliminary ultrasound data may comprise B-mode ultrasound data and/or color Doppler ultrasound data.

In step 120, an anatomical feature is identified within the region of interest based on the preliminary ultrasound data.

In other words, the preliminary ultrasound data is used to identify an anatomical feature within the region of interest for further imaging. For example, the anatomical feature may be a valve of the heart, such as the mitral valve or the aortic valve, or a fetus. The preliminary ultrasound data may be used to find a location and/or orientation of the anatomical feature within the region of interest.

In step 130, a first imaging position and one or more additional imaging positions are determined based on the anatomical feature.

In other words, the preliminary ultrasound data obtained during the scouting scan is used to derive anatomical information from the region of interest, which may then be used to guide the movement of an ultrasonic probe for capturing 3D, or 4D, ultrasound data based on the identified anatomical feature.

This may, for example, be performed by selecting 2D imaging planes from the preliminary ultrasound data likely to contain an anatomical feature and selecting an anatomical feature that overlaps between two or more ultrasound probe positions for centering the 3D volumes to be acquired. This selection may be performed manually, by way of receiving a user input, or automatically through model-based best plane identification in 3D mode, for example, using an annotated model of a heart.

In step 140, a first 3D ultrasound image is obtained from the first imaging position and one or more additional 3D ultrasound images are obtained from the one or more additional imaging positions. The images are obtained such that a portion of the first 3D ultrasound image overlaps a portion of each of the one or more additional 3D ultrasound images and the overlapping region comprises the anatomical feature.

The acquisition of these 3D ultrasound images based on anatomical context provides for more accurate fusion of the first 3D ultrasound image and the one or more additional 3D ultrasound images to form the composite 3D ultrasound image. Further, the method provides for an improvement in image quality and the systematic acquisition of relevant 2D planes facilitates the objective interpretation of the 3D composite ultrasound image.

As discussed above, the first 3D ultrasound image and the one or more additional 3D ultrasound image are obtained from first and additional imaging positions, respectively. Accordingly, the ultrasonic probe used to acquire the 3D ultrasound images will have to move from the first imaging position to the one or more additional imaging positions.

The ultrasonic probe may include an inertial sensor in order to measure the movement of the probe, and of the subject, which may then be accounted for in order to remove image artifacts relating to the motion of the probe during ultrasound acquisition. The inertial sensor may be placed in such a way that the magnetic field generated by the motor of the ultrasonic probe during 3D ultrasound acquisition mode doesn't affect the sensor.

Alternatively, an electro-magnetic tracker or a leap tracker may also be used in the ultrasonic probe for tracking the motion of the probe. Ultrasound data and the data from the motion sensors are acquired simultaneously. The rotation information from the motion sensor is input to the spatial registration algorithm, discussed below, for volume fusion. Common anatomical landmarks in the neighboring 3D volumes from overlapping regions are identified, which may then be used for translation correction in the spatial registration algorithm, based on the motion sensor data.

In step 150, spatial registration is performed between the first 3D ultrasound image and the one or more additional 3D ultrasound images based on the anatomical feature.

In other words, the location and/or orientation of the first 3D ultrasound image is determined relative to the one or more additional 3D ultrasound images and vice versa.

Performing the spatial registration may include generating a 3D point cloud within the first 3D ultrasound image and the one or more additional 3D ultrasound images, wherein the 3D point cloud represents a surface within the first 3D ultrasound image and a surface within the one or more additional 3D ultrasound images.

The 3D point cloud generation may be performed as follows. A specific anatomy model, such as a cardiac model or a fetal model, may be used to drive a classification module for identifying slices/volumes of interest within the 3D ultrasound images. This reduces the search space for anatomy driven point cloud computation.

A segmentation module may then be used to generate an anatomy driven heat map on the slices/volumes selected by the classification module to produce a 3D point cloud within the 3D ultrasound images. This bi-directional approach reduces the search space needed for point cloud generation, thereby increasing the computational efficiency of the method.

A probability map may be generated based on the 3D point cloud, the probability map representing a confidence value of the anatomical feature occupying a given point within the first 3D ultrasound image and the one or more additional 3D ultrasound images. An anatomical feature may be automatically identified when the confidence level exceeds a predetermined threshold value.

Confidence values derived from the above mentioned process may be used to create a 3D confidence map of the anatomical feature, which may be used as a deciding factor to blend the volumes. In other words, a confidence map may improve the visualization of the anatomical feature (even in pixel level) leading to better selective amalgamation of the 3D ultrasound images.

The spatial registration may be based on a machine learning algorithm, which may for example be adapted to perform bi-level stitching on the first 3D ultrasound image and the one or more additional 3D ultrasound images, based on the 3D point cloud.

In other words, a machine learning (and in particular, a deep learning) driven, anatomical probability based, 3D point cloud formation on the acquired 3D ultrasound images may be used to perform anatomy specific stitching using non-rigid registration techniques.

A point cloud based stitching, such as the technique discussed in Elbaz et al., 3D Point Cloud Registration for Localization using a Deep Neural Network Auto-Encoder, IEEE Conf CVPR, 2017, pp. 4631-4640, may be employed for performing non-rigid registration between the first 3D ultrasound image and the second 3D ultrasound image. A probability map, such as the one discussed above, of overlapped voxels within the overlapping portion of the 3D ultrasound images may act as a pivotal factor for final voxel selection in the stitched volume of the composite 3D ultrasound image. The use of the probability map increases the accuracy of the anatomical representation of the composite 3D ultrasound image.

Typical stitching methods, such as mono-directional successive target-source pair based registration, may be replaced by a more robust stitching method that leverages bidirectional-neighborhood topology.

In other words, spatial registration is not performed cumulatively along the direction of volume acquisition. Rather, the positioning of the ultrasound probe and its neighborhood influence is an indicator of target-source pair selection. Hence, a bidirectional registration scheme may be employed in the spatial registration, thereby reducing the error propagation from both acquisition directions.

In step 160, the first 3D ultrasound image and the one or more additional 3D ultrasound images are blended based on the spatial registration, thereby generating a composite 3D ultrasound image.

As discussed above, a probability map may be generated for the first 3D ultrasound image and the one or more additional 3D ultrasound images during the spatial registration step. This may be used as the basis for a 3D confidence map of the overlapping portion of 3D ultrasound images.

The blending may be performed using Poisson blending, which is a gradient domain image processing technique. Gradient domain image processing techniques operate on the differences between neighboring pixels, rather than on the pixel values directly.

The blending may also be performed using any suitable blending technique. For example, the blending may be performed using: alpha blending; pyramidal blending; Laplacian blending; and the like.

In addition to the spatial registration step, it is possible to employ a machine learning, or deep learning, algorithm in the blending step. For example, a machine learning algorithm may be trained to recognize structures and combine the 3D ultrasound images in a given manner depending on the recognized structure.

In step 170, a motion of the anatomical feature may be determined based on the composite 3D ultrasound image. The determining of the motion of the anatomical feature is described further below with reference to FIG. 4.

It should be noted that, although the example described below with reference to FIG. 3 describes the generation of a composite 3D ultrasound image based on two 3D ultrasound images, the composite 3D ultrasound image may be generated based on any number of acquired 3D ultrasound images.

For example, three 3D ultrasound images may be acquired form three different imaging positions in order to generate the composite 3D ultrasound image.

Put another way, a plurality of 3D ultrasound images may be blended in order to generate the composite 3D ultrasound image.

Figure 3:
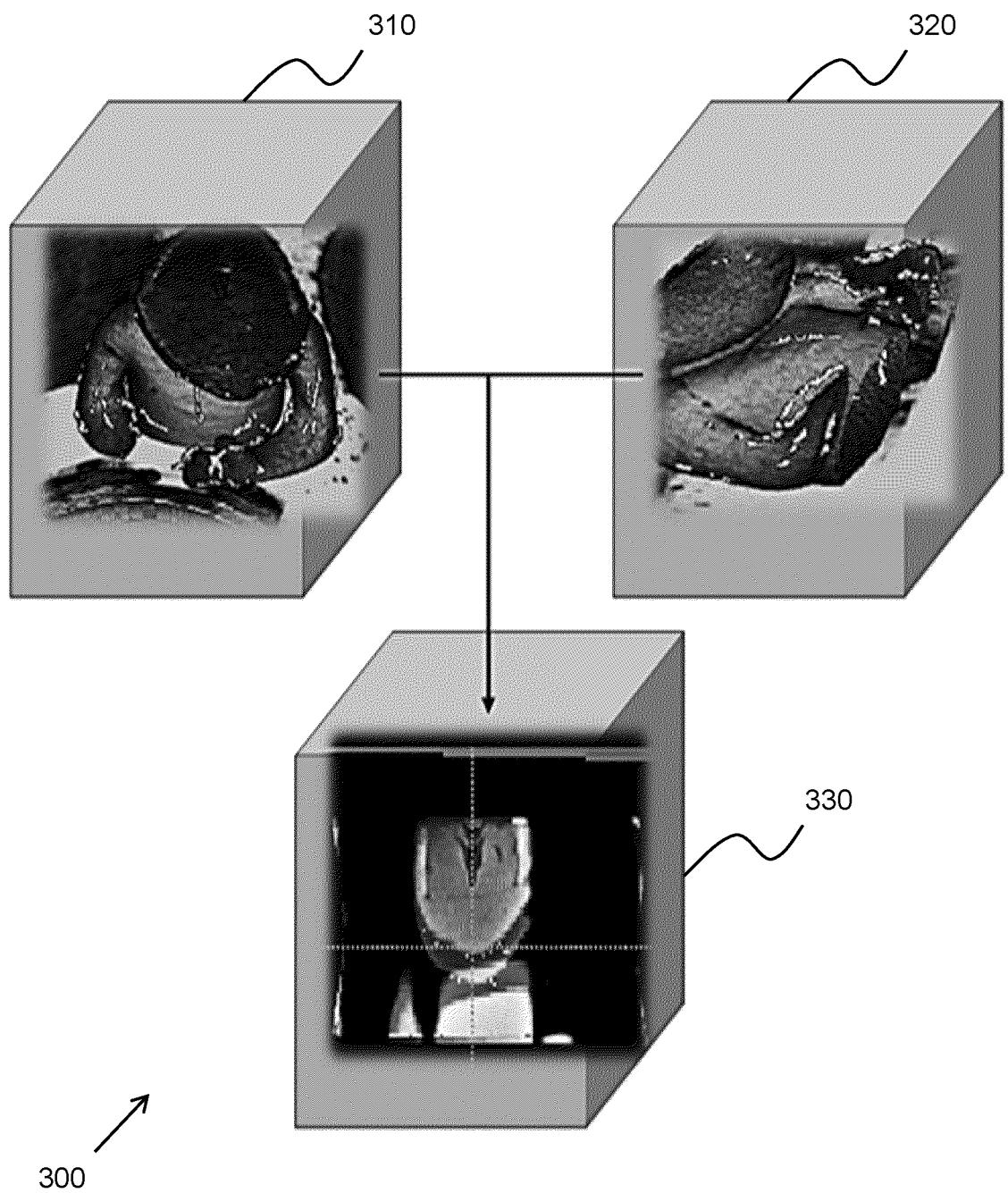
FIG. 3 shows a schematic representation of 3D point cloud based volume stitching according to the method of FIG. 2.

FIG. 3 shows a schematic representation 300 of 3D point cloud based volume stitching according to the method described above.

FIG. 3 shows a first 3D ultrasound image 310 and an additional 3D ultrasound image 320 to be used to generate the composite 3D ultrasound image 330. The first 3D ultrasound image and the additional 3D ultrasound images show two perspectives of an anatomical object with an overlapping portion comprising a common anatomical feature.

Two modules are applied to the first 3D ultrasound image and the second 3D ultrasound image, namely, a classification module and a segmentation module. The classification module identifies the presence of relevant objects in each 2D slice of a 3D volume and the segmentation module localizes an object in the 2D slices selected by the classification module in the form of a point cloud.

The classification module acts to restrict the segmentation module to run within the vicinity of the object of interest, or anatomical feature. In turn this will isolate the object whose surface plot is represented by the point cloud.

Thus, a 3D point cloud is generated in each of the 3D ultrasound images before they are blended to form the composite 3D ultrasound image, a 2D slice (ultrasound image 330) shown in FIG. 3.

Figure 4:
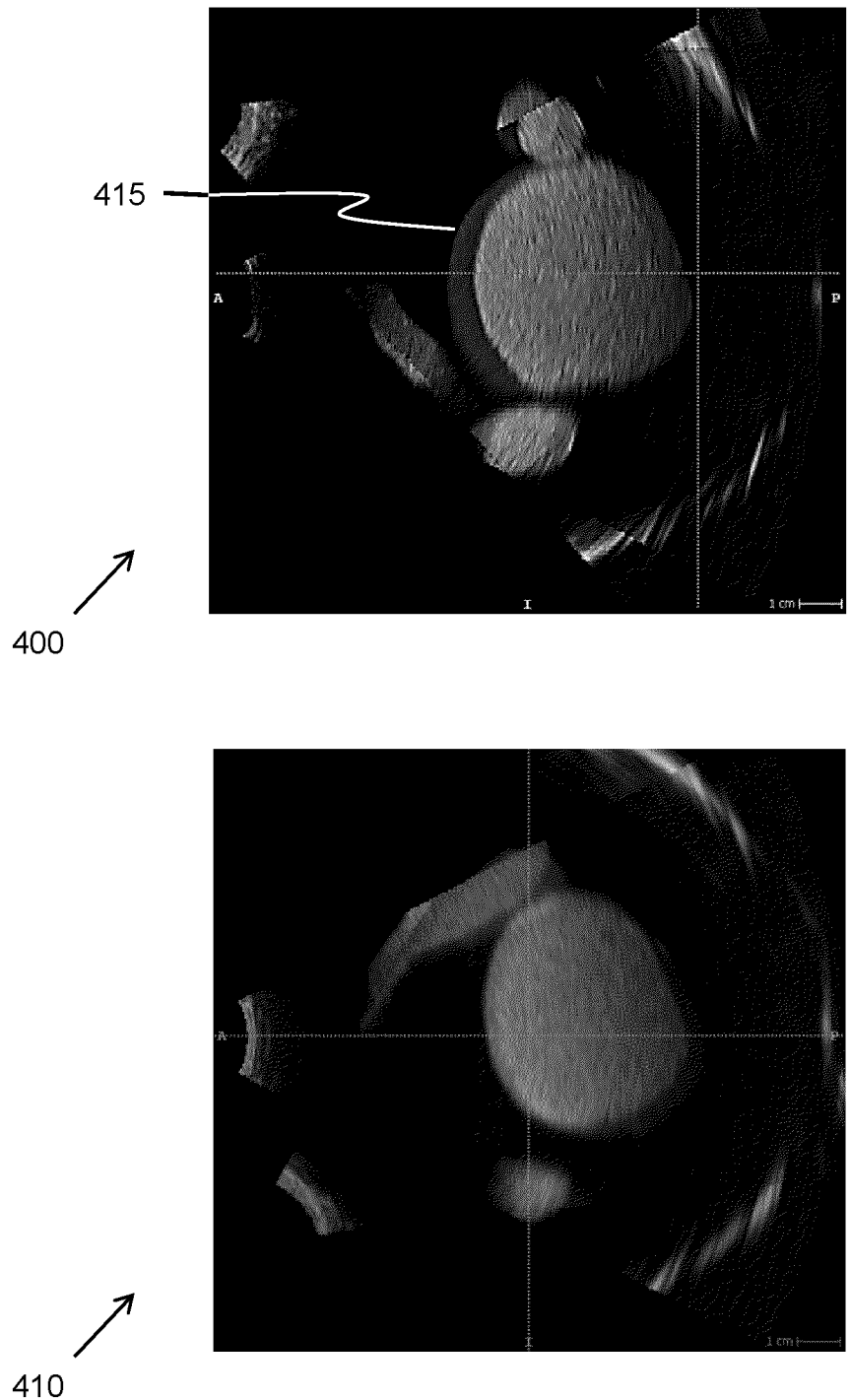
FIG. 4 shows a comparison between composite images generated using rigid and non-rigid stitching methods.

FIG. 4 shows a comparison between a composite image generated using a rigid stitching method and a composite image generated using a non-rigid stitching method.

The use of rigid registration while performing volume stitching may cause shadow artifacts on moving anatomical structures within the images, such as a fetus (for example a hand or a leg) or a heart valve, due to their natural movements. An example of a shadow artifact 415 is shown in image 400.

In comparison, non-rigid registration can eliminate shadow artifacts, such as shadow artifact 415. Image 410 shows a composite image of the same anatomical feature as image 400; however, as image 410 is generated using a non-rigid stitching method, the presence of shadow artifacts in the final image is significantly reduced.

As stated above, shadow artifacts may arise in the composite 3D ultrasound image due to movement of the anatomical feature. These shadow artifacts may be captured through applying non-rigid transformation matrices to the composite 3D ultrasound image in order to do a movement count. In other words, this apparent registration anomaly/error may be used to track anatomical movements in 3D.

In the case of 4D ultrasound acquisitions, which are simply a large number of adjacent 3D volumes, the non-rigid transformation matrix may provide probabilistic loci of the movement of the anatomical feature, which may be used for quantifying/tracking the anatomical movement.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A method for obtaining a composite 3D ultrasound image of a region of interest, the method comprising:
   obtaining preliminary ultrasound data from a region of interest of a subject;
   identifying an anatomical feature within the region of interest based on the preliminary ultrasound data;
   determining a first imaging position and one or more additional imaging positions based on the anatomical feature;
   obtaining a first three-dimensional (3D) ultrasound image from the first imaging position and one or more additional 3D ultrasound images from the one ore more additional imaging positions, wherein a portion of the first 3D ultrasound image overlaps a portion of the one or more additional 3D ultrasound images, thereby forming an overlapping portion and wherein the overlapping portion comprises the anatomical feature;
   performing spatial registration between the first 3D ultrasound image and the one or more additional 3D ultrasound images based on the anatomical feature, wherein performing spatial registration comprises:
      generating a 3D point cloud within the first 3D ultrasound image and the one or more additional 3D ultrasound images, wherein the 3D point cloud represents a surface within the first 3D ultrasound image and a surface within the one or more additional 3D ultrasound images; and
      generating a probability map based on the 3D point cloud, the probability map representing a confidence value of the anatomical feature occupying a given point within the first 3D ultrasound image and the one or more additional 3D ultrasound images; and
   blending the first 3D ultrasound image and the one or more additional 3D ultrasound images based on the spatial registration, thereby generating a composite 3D ultrasound image, wherein blending the first 3D ultrasound image and the one or more additional 3D ultrasound images is based on the probability map.

2. The method as claimed in claim 1, wherein the method further comprises determining a motion of the anatomical feature based on the composite 3D ultrasound image.

3. The method as claimed in claim 2, wherein determining the motion of the anatomical feature comprises:
   applying a non-rigid transformation matrix to the composite 3D ultrasound image; and
   identifying an artifact based on the transformed composite 3D ultrasound image.

4. The method as claimed in claim 3, wherein determining the motion of the anatomical feature comprises tracking the artifact.

5. The method as claimed in claim 1, wherein performing spatial registration comprises using a machine learning algorithm.

6. The method as claimed in claim 5, wherein the machine learning algorithm is adapted to perform bi-level stitching based on the 3D point cloud.

7. The method as claimed in claim 1, wherein performing spatial registration comprises identifying a location of the anatomical feature within the first 3D ultrasound image and the one or more additional 3D ultrasound images when a confidence value is greater than a predetermined value.

8. The method as claimed in claim 1, wherein blending the first 3D ultrasound image and the one or more additional 3D ultrasound images comprises generating a 3D confidence map of the overlapping portion based on the probability map.

9. The method as claimed in claim 1, wherein blending the first 3D ultrasound image and the one or more additional 3D ultrasound images comprises applying Poisson blending the first 3D ultrasound image and the one or more additional 3D ultrasound images.

10. A tangible non-transitory computer readable medium that stores code, which when executed by a processor, causes the processor to:
   obtain preliminary ultrasound data from a region of interest of a subject;
   identify an anatomical feature within the region of interest based on the preliminary ultrasound data;
   determine a first imaging position and one or more additional imaging positions based on the anatomical feature;
   obtain a first three-dimensional (3D) ultrasound image from the first imaging position and one or more additional 3D ultrasound images from the one or more additional imaging positions, wherein a portion of the first 3D ultrasound image overlaps a portion of the one or more additional 3D ultrasound images, thereby forming an overlapping portion and wherein the overlapping portion comprises the anatomical feature;

perform spatial registration between the first 3D ultrasound image and the one or more additional 3D ultrasound images based on the anatomical feature, wherein performing spatial registration comprises: generating a 3D point cloud within the first 3D ultrasound image and the one or more additional 3D ultrasound images, wherein the 3D point cloud represents a surface within the first 3D ultrasound image and a surface within the one or more additional 3D ultrasound images; and generating a probability map based on the 3D point cloud, the probability map representing a confidence value of the anatomical feature occupying a given point within the first 3D ultrasound image and the one or more additional 3D ultrasound images; and blend the first 3D ultrasound image and the one or more additional 3D ultrasound images based on the spatial registration, thereby generating a composite 3D ultrasound image, wherein blending the first 3D ultrasound image and the one or more additional 3D ultrasound images is based on the probability map.

11. An ultrasound system, comprising:
an ultrasound probe;
a processor;
a tangible, non-transitory computer readable medium that stores code, which when executed by the processor, causes the processor to:
obtain preliminary ultrasound data from a region of interest of a subject;
identify an anatomical feature within the region of interest based on the preliminary ultrasound data;
determine a first imaging position and one or more additional imaging positions based on the anatomical feature;
obtain a first three-dimensional (3D) ultrasound image from the first imaging position and one or more additional 3D ultrasound images from the one or more additional imaging positions, wherein a portion of the first 3D ultrasound image overlaps a portion of the one or more additional 3D ultrasound images, thereby forming an overlapping portion and wherein the overlapping portion comprises the anatomical feature;
perform spatial registration between the first 3D ultrasound image and the one or more additional 3D ultrasound images based on the anatomical feature, wherein performing spatial registration comprises: generating a 3D point cloud within the first 3D ultrasound image and the one or more additional 3D ultrasound images, wherein the 3D point cloud represents a surface within the first 3D ultrasound image and a surface within the one or more additional 3D ultrasound images; and generating a probability map based on the 3D point cloud, the probability map representing a confidence value of the anatomical feature occupying a given point within the first 3D ultrasound image and the one or more additional 3D ultrasound images; and blend the first 3D ultrasound image and the one or more additional 3D ultrasound images based on the spatial registration, thereby generating a composite 3D ultrasound image, wherein blending the first 3D ultrasound image and the one or more additional 3D ultrasound images is based on the probability map.

12. The ultrasound system as claimed in claim 11, wherein the ultrasound probe is adapted to acquire four-dimensional (4D) data.

13. The ultrasound system as claimed in claim 11, wherein the ultrasound probe comprises one or more of:
a motion sensor;
an electromagnetic tracker; and
a leap tracker.

14. The ultrasound system as claimed in claim 11, wherein when the spatial registration is performed, the code comprises a machine learning algorithm.

15. The ultrasound system as claimed in claim 14, wherein the machine learning algorithm is adapted to perform bi-level stitching based on the 3D point cloud.

16. The ultrasound system as claimed in claim 11, wherein the code further causes the processor to determine a motion of the anatomical feature based on the composite 3D ultrasound image.

17. The ultrasound system as claimed in claim 16, wherein when the motion of the anatomical feature is determined, the code further causes the processor to:
apply a non-rigid transformation matrix to the composite 3D ultrasound image; and
identify an artifact based on the transformed composite 3D ultrasound image.

18. The ultrasound system as claimed in claim 16, wherein when the motion of the anatomical feature is determined, the code causes the processor to comprises track an artifact.

19. The ultrasound system as claimed in claim 11, wherein when the spatial registration is performed, the code further causes the processor to identify a location of the anatomical feature within the first 3D ultrasound image and the one or more additional 3D ultrasound images when the confidence value is greater than a predetermined value.

20. The ultrasound system as claimed in claim 11, wherein blending the first 3D ultrasound image and the one or more additional 3D ultrasound images comprises generating a 3D confidence map of the overlapping portion based on the probability map.

* * * * *